US009011471B2

United States Patent
Timm et al.

(10) Patent No.: US 9,011,471 B2
(45) Date of Patent: Apr. 21, 2015

(54) SURGICAL INSTRUMENT WITH PIVOTING COUPLING TO MODULAR SHAFT AND END EFFECTOR

(75) Inventors: Richard W. Timm, Cincinnati, OH (US); Kyle P. Moore, Mason, OH (US); Gregory W. Johnson, Milford, OH (US); John B. Schulte, West Chester, OH (US); Daniel J. Mumaw, Johannesburg (ZA); David A. Witt, Maineville, OH (US); Gregory A. Trees, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/270,667

(22) Filed: Oct. 11, 2011

(65) Prior Publication Data

US 2012/0116394 A1 May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 17/32* (2006.01)
*A61B 18/14* (2006.01)
(Continued)

(52) U.S. Cl.
CPC .............. *A61B 18/1442* (2013.01); *H01M 2/26* (2013.01); *H01M 2/10* (2013.01); *A61B 18/1206* (2013.01); *A61B 17/00234* (2013.01); *A61B 17/064* (2013.01); *A61B 17/285* (2013.01); *A61B 17/320068* (2013.01); *A61B 17/320092* (2013.01); *A61B 18/00* (2013.01);
(Continued)

(58) Field of Classification Search
USPC .......................... 606/27, 33, 45, 169; 604/22
See application file for complete search history.

(56) References Cited

U.S. PATENT DOCUMENTS 1,754,806 A * 4/1930 Stevenson ..................... 606/174
3,297,192 A 1/1967 Swett
(Continued)

FOREIGN PATENT DOCUMENTS

| DE | 102008051866 | 10/2010 |
|---|---|---|
| DE | 102009013034 | 10/2010 |

(Continued)

OTHER PUBLICATIONS

U.S. Appl. No. 13/151,471, filed Jun. 2, 2011, Stulen.
(Continued)

*Primary Examiner* — Katherine M Shi

(57) ABSTRACT

A surgical instrument comprises a body and a shaft assembly. The body includes an energy source such as an ultrasonic transducer. The shaft assembly comprises an end effector and a transmission member such as an acoustic waveguide. The end effector may include a harmonic blade and a pivoting clamp member. One or both of the body or the shaft assembly includes a pivot feature. The pivot feature is operable to secure the shaft assembly to the body. The pivot feature may include a bar defining a pivot axis about which the shaft assembly pivots to secure the shaft assembly to the body. The pivot axis may be perpendicular to a longitudinal axis defined by the shaft assembly. The pivot feature may also include a pivoting cover configured to cover a recess in the body in which a proximal portion of the shaft assembly is received.

17 Claims, 8 Drawing Sheets

(51) Int. Cl.
  *A61B 17/00* (2006.01)
  *A61B 18/00* (2006.01)
  *A61B 18/04* (2006.01)
  *H02J 7/00* (2006.01)
  *H01M 2/26* (2006.01)
  *H01M 2/10* (2006.01)
  *A61B 18/12* (2006.01)
  *A61B 17/064* (2006.01)
  *A61B 17/285* (2006.01)
  *A61B 19/00* (2006.01)
  *A61B 17/29* (2006.01)

(52) U.S. Cl.
  CPC ............... *A61B 18/04* (2013.01); *A61B 18/12* (2013.01); *A61B 18/1233* (2013.01); *A61B 18/14* (2013.01); *A61B 18/1445* (2013.01); *A61B 19/38* (2013.01); *A61B 2017/00084* (2013.01); *A61B 2017/00398* (2013.01); *A61B 2017/0046* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/2929* (2013.01); *A61B 2017/293* (2013.01); *A61B 2017/2931* (2013.01); *A61B 2017/2933* (2013.01); *A61B 2017/294* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2019/4815* (2013.01); *A61B 2019/4868* (2013.01); *A61B 2019/4873* (2013.01); *H02J 7/0045* (2013.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | DiMatteo et al. |
| 6,056,735 A | 5/2000 | Okada et al. |
| 6,063,098 A * | 5/2000 | Houser et al. ............... 606/169 |
| 6,066,151 A | 5/2000 | Miyawaki et al. |
| 6,083,191 A | 7/2000 | Rose |
| 6,099,537 A * | 8/2000 | Sugai et al. ............... 606/143 |
| 6,165,191 A | 12/2000 | Shibata et al. |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,514,267 B2 | 2/2003 | Jewett |
| 6,520,185 B1 | 2/2003 | Bommannan et al. |
| 6,561,983 B2 | 5/2003 | Cronin et al. |
| 6,609,414 B2 | 8/2003 | Mayer et al. |
| 6,623,500 B1 | 9/2003 | Cook et al. |
| 6,626,901 B1 | 9/2003 | Treat et al. |
| 6,647,281 B2 | 11/2003 | Morency |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,717,193 B2 | 4/2004 | Olewine et al. |
| 6,730,042 B2 | 5/2004 | Fulton et al. |
| 6,758,855 B2 | 7/2004 | Fulton, III et al. |
| 6,761,698 B2 | 7/2004 | Shibata et al. |
| 6,783,524 B2 | 8/2004 | Anderson et al. |
| 6,815,206 B2 | 11/2004 | Lin et al. |
| 6,821,671 B2 | 11/2004 | Hinton et al. |
| 6,838,862 B2 | 1/2005 | Luu |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 7,031,155 B2 | 4/2006 | Sauciuc et al. |
| 7,077,853 B2 | 7/2006 | Kramer et al. |
| 7,083,589 B2 | 8/2006 | Banko et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |

(56) References Cited

U.S. PATENT DOCUMENTS

| | | |
|---|---|---|
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckal et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 | 7/2009 | Wenger et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,776,037 B2 | 8/2010 | Odom |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,564,242 B2 | 10/2013 | Hansford et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2002/0103496 A1* | 8/2002 | Harper et al. ................ 606/169 |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0247620 A1* | 11/2006 | Bourne et al. ................ 606/41 |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0234708 A1* | 9/2008 | Houser et al. ................ 606/169 |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1* | 4/2009 | Price et al. ................ 606/206 |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumara et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1* | 1/2011 | Schultz et al. ................ 600/109 |
| 2011/0015660 A1 | 1/2011 | Wiener et al. |
| 2011/0058982 A1 | 3/2011 | Kaneko |
| 2011/0077514 A1 | 3/2011 | Ulric et al. |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |

(56) References Cited

U.S. PATENT DOCUMENTS

| | | | |
|---|---|---|---|
| 2011/0224668 | A1 | 9/2011 | Johnson et al. |
| 2011/0247952 | A1 | 10/2011 | Hebach et al. |
| 2012/0179036 | A1 | 7/2012 | Patrick et al. |
| 2012/0265230 | A1 | 10/2012 | Yates et al. |
| 2012/0283732 | A1 | 11/2012 | Lam |
| 2012/0292367 | A1 | 11/2012 | Morgan et al. |
| 2013/0085330 | A1 | 4/2013 | Ramamurthy et al. |
| 2013/0085332 | A1 | 4/2013 | Ramamurthy et al. |
| 2013/0085397 | A1 | 4/2013 | Ramamurthy et al. |
| 2013/0090528 | A1 | 4/2013 | Ramamurthy et al. |
| 2013/0090530 | A1 | 4/2013 | Ramamurthy et al. |
| 2013/0090552 | A1 | 4/2013 | Ramamurthy et al. |
| 2013/0116690 | A1 | 5/2013 | Unger et al. |

FOREIGN PATENT DOCUMENTS

| | | | |
|---|---|---|---|
| EP | 0897696 | A1 | 2/1999 |
| EP | 0947167 | A1 | 10/1999 |
| EP | 1330991 | A1 | 7/2003 |
| EP | 1525853 | A2 | 4/2005 |
| EP | 1535585 | A2 | 6/2005 |
| EP | 1684396 | A2 | 7/2006 |
| EP | 1721576 | A1 | 11/2006 |
| EP | 1743592 | A1 | 1/2007 |
| EP | 1818021 | A1 | 8/2007 |
| EP | 1839599 | | 10/2007 |
| EP | 1868275 | A2 | 12/2007 |
| EP | 1886637 | A1 | 2/2008 |
| EP | 1943976 | A2 | 7/2008 |
| EP | 1970014 | | 9/2008 |
| EP | 1997439 | A2 | 12/2008 |
| EP | 2027819 | A1 | 2/2009 |
| EP | 2090256 | A2 | 8/2009 |
| EP | 2105104 | A2 | 9/2009 |
| EP | 2165660 | A2 | 3/2010 |
| EP | 2218409 | A1 | 8/2010 |
| EP | 2243439 | A1 | 10/2010 |
| EP | 2345454 | A1 | 7/2011 |
| GB | 2425874 | | 11/2006 |
| GB | 2440566 | A | 2/2008 |
| WO | WO 97/24072 | | 7/1997 |
| WO | WO 00/65682 | | 2/2000 |
| WO | WO 03/013374 | | 2/2003 |
| WO | WO 03/020139 | | 3/2003 |
| WO | WO 2004/113991 | | 12/2004 |
| WO | WO 2005/079915 | | 9/2005 |
| WO | WO 2006/023266 | | 3/2006 |
| WO | WO 2007/004515 | | 1/2007 |
| WO | WO 2007/024983 | | 3/2007 |
| WO | WO 2007/090025 | | 8/2007 |
| WO | WO 2007/137115 | | 11/2007 |
| WO | WO 2007/137304 | | 11/2007 |
| WO | WO 2008/071898 | | 6/2008 |
| WO | WO 2008/102154 | | 8/2008 |
| WO | WO 2008/107902 | | 9/2008 |
| WO | WO 2008/131357 | | 10/2008 |
| WO | WO 2009/018409 | | 2/2009 |
| WO | WO 2009/046394 | | 4/2009 |
| WO | WO 2009/070780 | | 6/2009 |
| WO | WO 2009/073608 | | 6/2009 |
| WO | WO 2010/030850 | | 3/2010 |
| WO | WO 2010/096174 | | 8/2010 |
| WO | WO 2011/059785 | | 5/2011 |
| WO | WO 2011/089270 | | 7/2011 |

OTHER PUBLICATIONS

U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filec Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
International Search Report and Written Opinion dated Jan. 26, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
International Search Report dated Jan. 12, 2012 for Application No. PCT/US2011/059226.

(56) References Cited

OTHER PUBLICATIONS

International Search Report dated Jan. 26, 2012 for Application No. PCT/US2011/059220.
International Search Report dated Feb. 1, 2012 for Application No. PCT/US2011/059223.
International Search Report dated May 29, 2012 for Application No. PCT/US2011/059358.
International Search Report and Written Opinion dated Jul. 6, 2012 for Application No. PCT/US2011/059381.
Office Action Non-Final dated Aug. 6, 2013 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Mar. 13, 2013 for U.S. Appl. No. 13/151,509.
Restriction Requirement dated Jun. 24, 2013 for U.S. Appl. No. 13/151,509.
Restriction Requirement dated Dec. 21, 2012 for U.S. Appl. No. 13/274,516.
Office Action Final dated Aug. 16, 2013 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Office Action Final, dated Aug. 29, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/276,660.
Office Action Non-Final dated Dec. 21, 2012 for U.S. Appl. No. 13/276,673.
Office Action Non-Final dated Aug. 19, 2013 for U.S. Appl. No. 13/276,673.
Restriction Requirement dated Feb. 6, 2013 for U.S. Appl. No. 13/276,687.
Office Action Non Final dated Jun. 12, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Office Action Final dated Jan. 29, 2014 for U.S. Appl. No. 13/151,509.
Restriction Requirement dated Jun. 11, 2014 for U.S. Appl. No. 13/151,512.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Final dated Jun. 12, 2014 for U.S. Appl. No. 13/274,516.
Office Action Non-Final dated Jan. 6, 2014 for U.S. Appl. No. 13/275,514.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Non-Final dated Nov. 21, 2013 for U.S. Appl. No. 13/271,352.
Office Action Non-Final dated Dec. 6, 2013 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
EP Communication dated Feb. 19, 2014 for Application No. EP 11781972.2.
International Preliminary Report on Patentability dated May 7, 2013 for Application No. PCT/US2011/059212.
International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCT/US2011/059218.
International Preliminary Report on Patentability dated May 7, 2013 for Application No. PCT/US2011/059220.
International Preliminary Report on Patentability dated May 7, 2013 for Application No. PCT/US2011/059222.

(56) References Cited

OTHER PUBLICATIONS

International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Notice of Allowance, dated Aug. 19, 2014 for U.S. Appl. No. 13/151,471.
US Office Action, Non-Final, dated Aug. 14, 2014 for U.S. Appl. No. 13/151,481.
US Office Action, Non-Final, dated Nov. 7, 2014 for U.S. Appl. No. 13/151,488.
US Office Action, Notice of Allowance, dated Aug. 6, 2014 for U.S. Appl. No. 13/151,498.
US Office Action, Non-Final, dated Nov. 6, 2014 for U.S. Appl. No. 13/151,503.
US Office Action, Non-Final, dated Jul. 9, 2014 for U.S. Appl. No. 13/151,509.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Restriction Requirement, dated Jul. 11, 2014 for U.S. Appl. No. 13/269,870.
US Office Action, Restriction Requirement, dated Jul. 9, 2014 for U.S. Appl. No. 13/270,684.
US Office Action, Non-Final, dated Oct. 9, 2014 for U.S. Appl. No. 13/270,684.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.

* cited by examiner

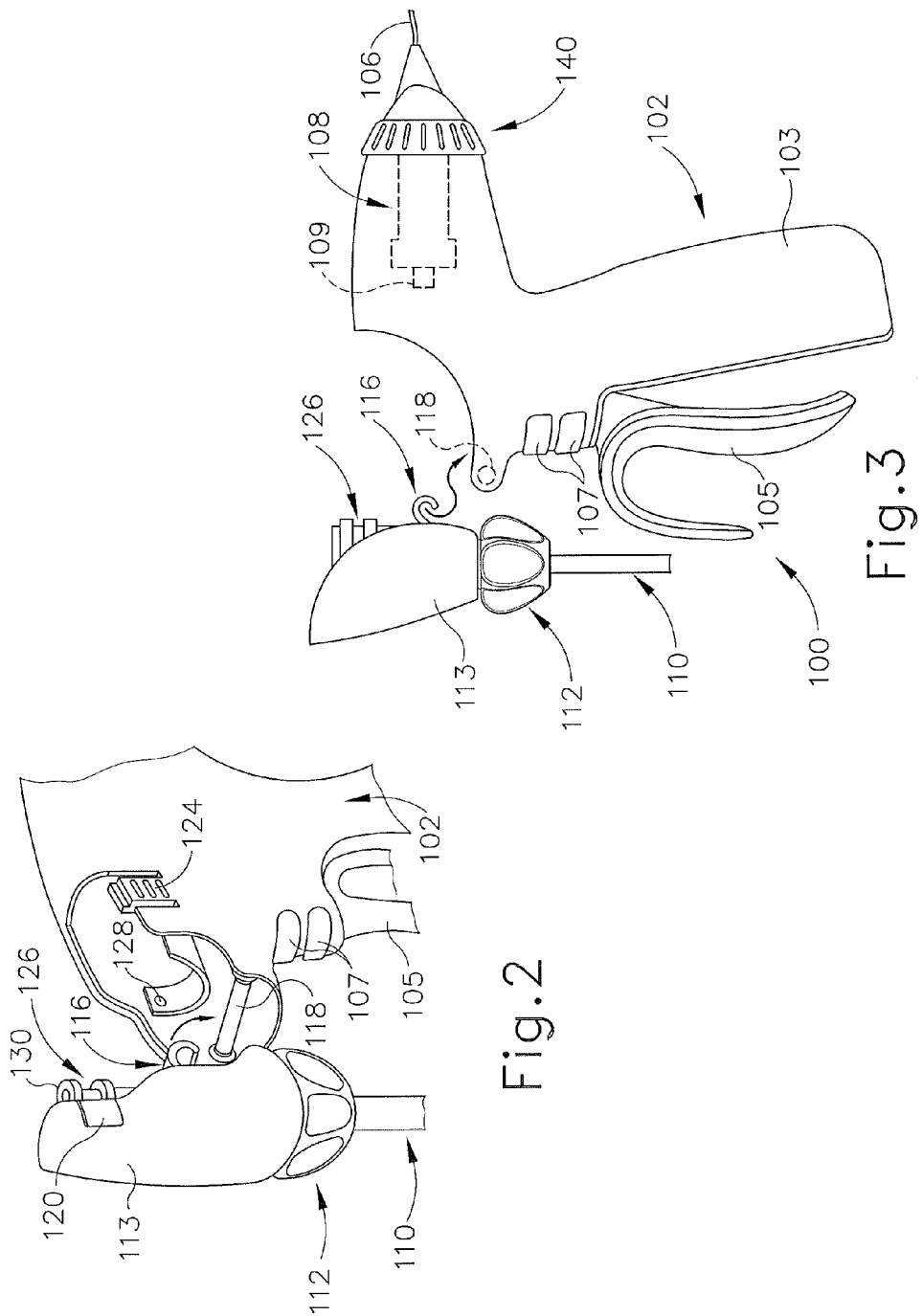

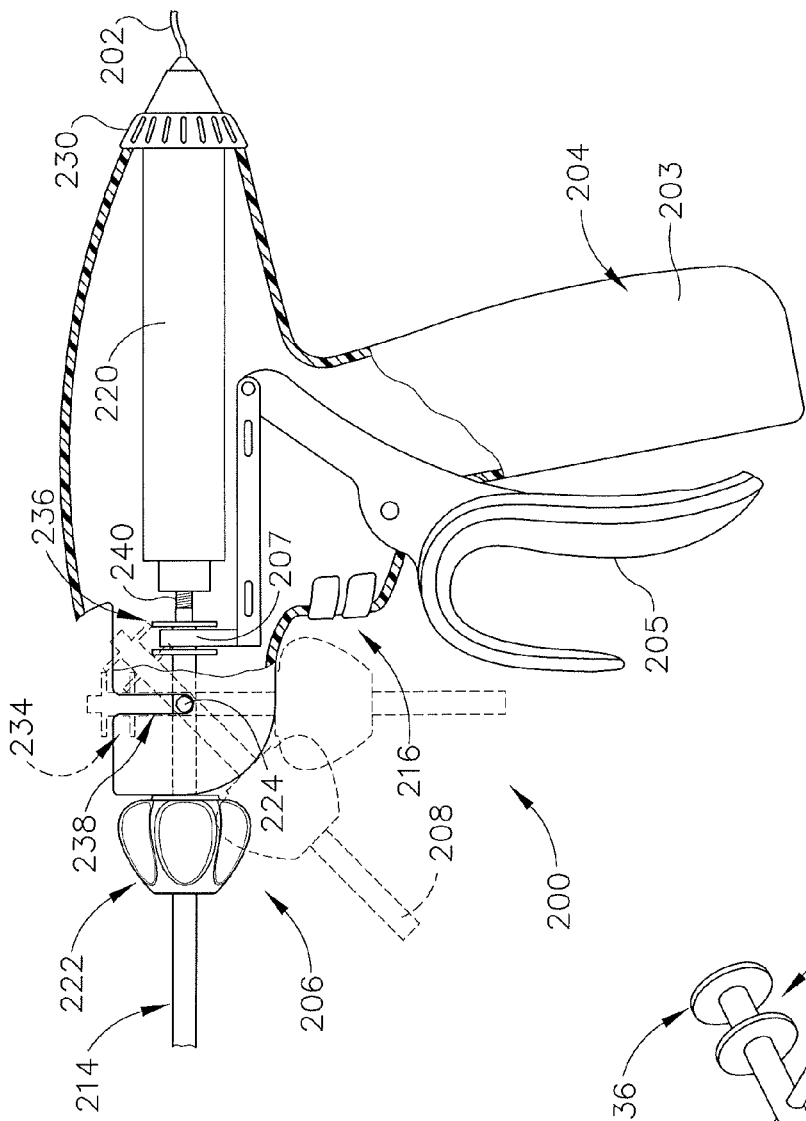
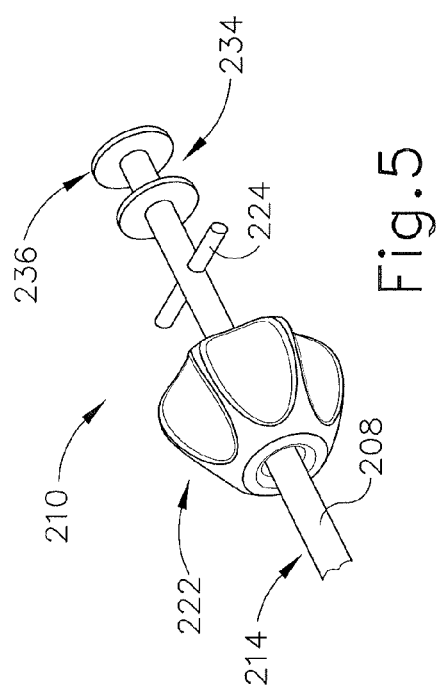
Fig. 4
Fig. 5

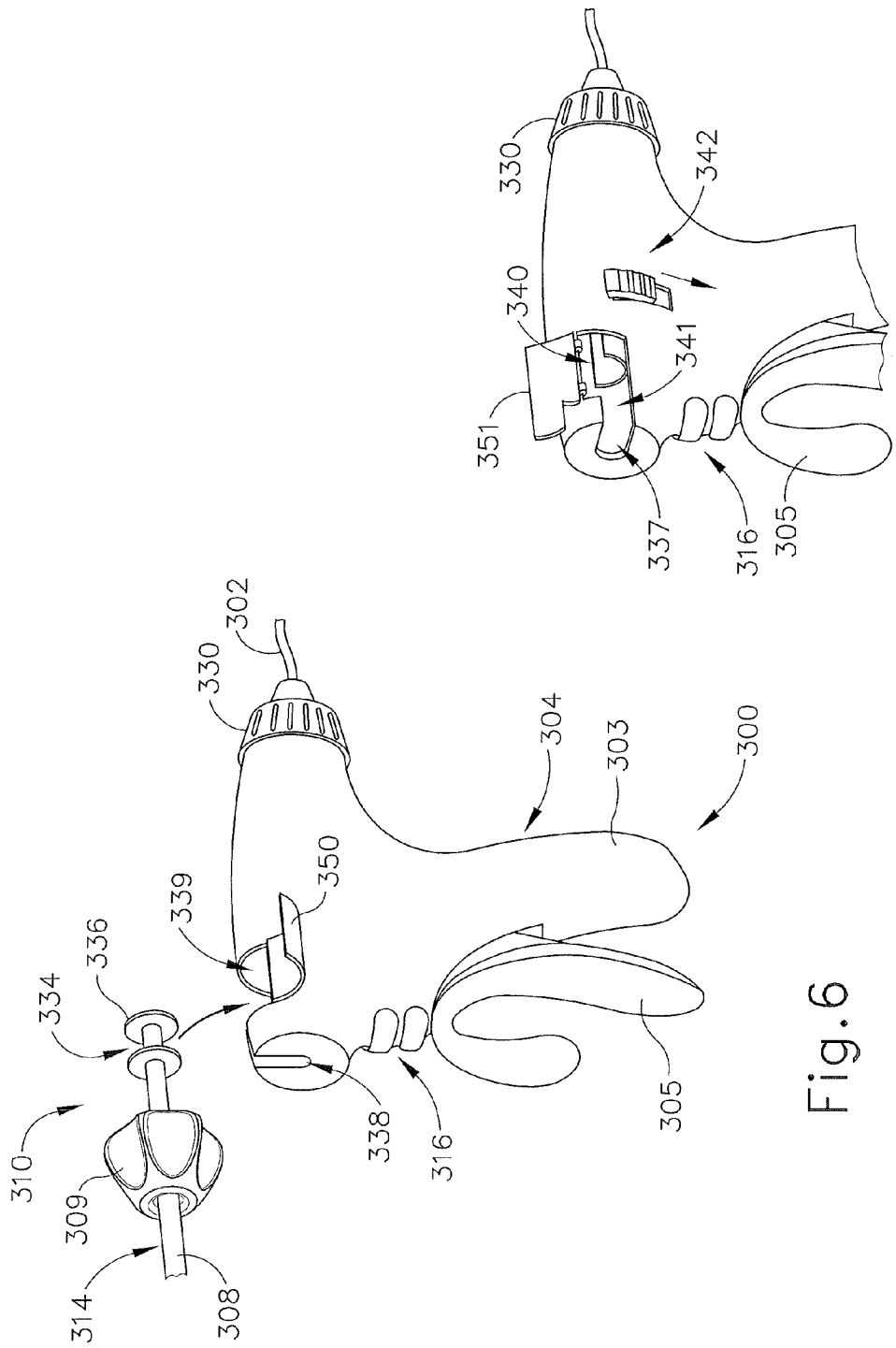

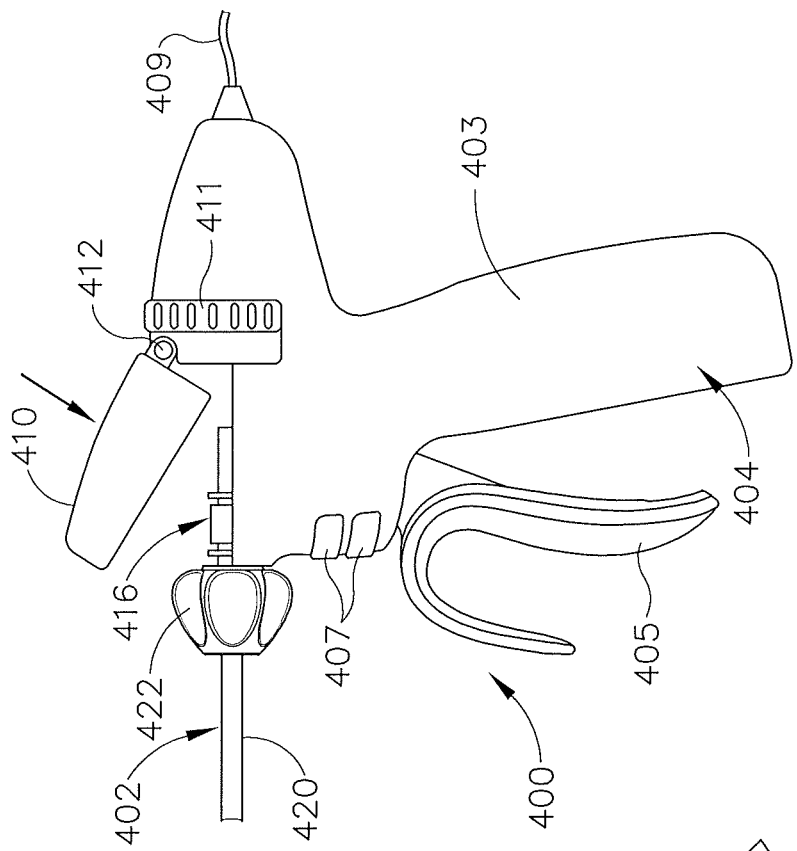
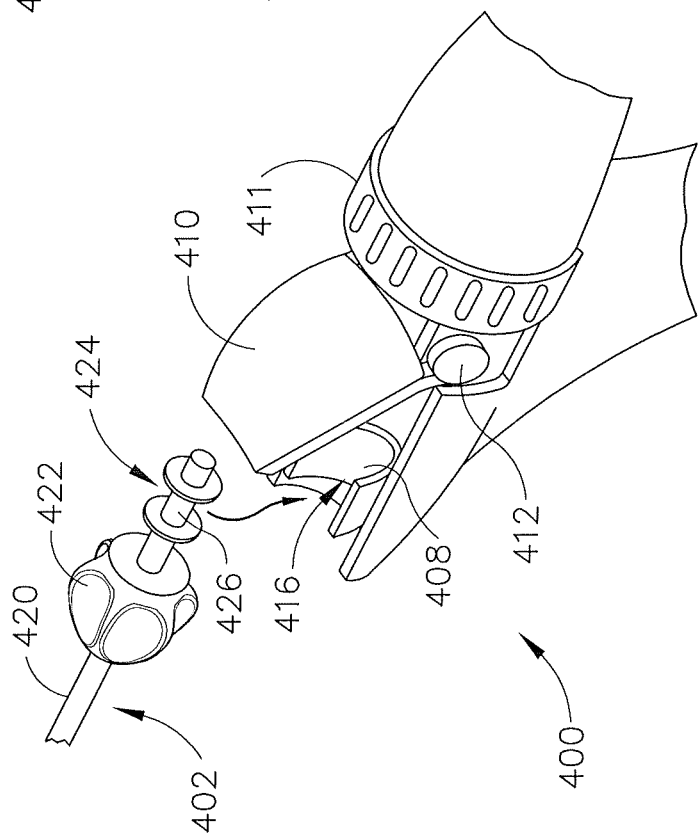
Fig. 9
Fig. 8

SURGICAL INSTRUMENT WITH PIVOTING COUPLING TO MODULAR SHAFT AND END EFFECTOR

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

A variety of surgical devices employ ultrasonic energy. In some instances, ultrasonic surgical instruments may provide substantially simultaneous cutting of tissue and hemostasis by coagulation, desirably minimizing patient trauma. Examples of ultrasonic surgical instruments are disclosed in U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0143797 (now U.S. Pat. No. 8,419,757), entitled "Cordless Hand-held Ultrasonic Cautery Cutting Device," published Jun. 4, 2009, the disclosure of which is incorporated by reference herein; U.S. Pub. No. 2010/0069940 entitled "Ultrasonic Device for Fingertip Control," published Mar. 18, 2010, the disclosure of which is incorporated by reference herein; and U.S. Pub. No. 2011/0015660, entitled "Rotating Transducer Mount for Ultrasonic Surgical Instruments," published Jan. 20, 2011, and issued as U.S. Pat. No. 8,461,744 on Jun. 11, 2013, the disclosures of which are incorporated by reference herein. Various ways in which ultrasonic surgical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Some other surgical instruments employ RF energy to assist in coagulation or sealing of tissue. Examples of RF surgical instruments are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218 (now U.S. Pat. No. 8,939,974), entitled "Surgical Instrument Comprising First and Second Drive Systems Actuatable by a Common Trigger Mechanism," published Apr. 14, 2011, the disclosure of which is incorporated by reference herein; and U.S. patent application Ser. No. 13/151,481, entitled "Motor Driven Electrosurgical Device with Mechanical and Electrical Feedback," filed Jun. 2, 2011, published as U.S. Pub. No. 2012/0116379, the disclosures of which are incorporated by reference herein Additional powered surgical instruments that include an end effector are disclosed in U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; and U.S. Pub. No. 2009/0209990 (now U.S. Pat. No. 8,657,174) entitled "Motorized Surgical Cutting and Fastening Instrument Having Handle Based Power Source," published Aug. 20, 2009, the disclosure of which is incorporated by reference herein.

As described in greater detail below, ultrasonic surgical instruments, RF electrosurgical instruments, and surgical cutting/stapling instruments (among other types of surgical instruments) may be constructed with modular parts such that parts can be readily replaced or otherwise changed by a user. For instance, such modularity may enable selection of different end effectors for different settings. In addition or in the alternative, replaceability may provide a dichotomy of reusable and disposable parts of a surgical instrument. In some settings (e.g., those where a handle assembly is re-used several times, etc.), it may be desirable to provide a mechanism for the quick and accurate exchange of disposable blade/tube assemblies being utilized in a reusable handle. Similarly, it may be desirable to facilitate the utilization of several disposable blade/tube assemblies during a single medical procedure or for several separate medical procedures.

While a variety of surgical instruments have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2 depicts a partial perspective view of an exemplary surgical instrument, with a shaft assembly detached and positioned for coupling with a handle assembly;

FIG. 3 depicts a side view of the exemplary surgical instrument of FIG. 2;

FIG. 4 depicts a partial cross-sectional view of another exemplary surgical instrument, showing a shaft assembly in various stages of coupling with a handle assembly;

FIG. 5 depicts a partial perspective view of the shaft assembly of the surgical instrument of FIG. 4;

FIG. 6 depicts a partial perspective view of an exemplary surgical instrument, with a shaft assembly detached and positioned for coupling with a handle assembly;

FIG. 7 depicts a partial perspective view of yet another exemplary surgical instrument, with a shaft assembly omitted;

FIG. 8 depicts a partial perspective view of still another exemplary surgical instrument, with a shaft assembly detached and positioned for coupling with a handle assembly;

FIG. 9 depicts a partial side view of the surgical instrument of FIG. 8, with the shaft assembly seated in the handle assembly;

Figure 1:
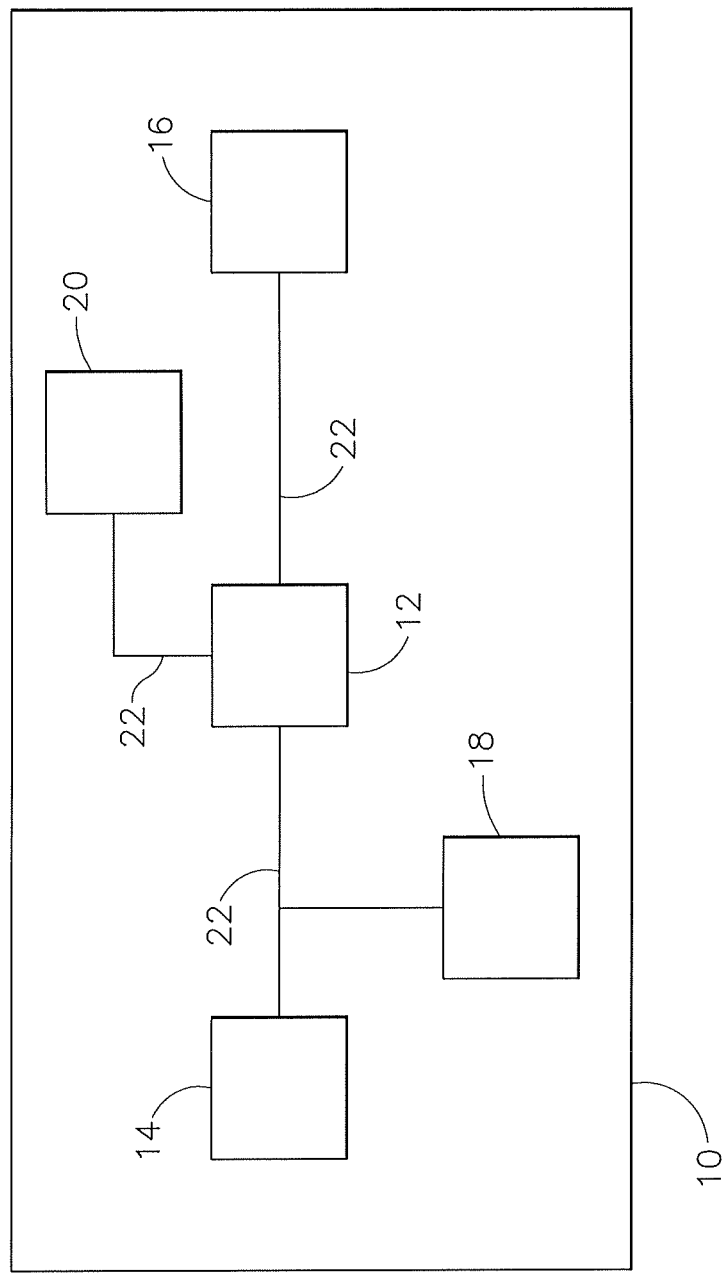
FIG. 1 depicts a schematic view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Surgical Instruments for Use With Disposable Blade/Tube Components Coupled to a Reusable Handle FIG. 1 shows components of an exemplary surgical instrument (10) in diagrammatic block form. As shown, surgical instrument (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from surgical instrument (10), which may further allow power source (14) to be readily recharged or reclaimed for resterilization and reuse. In addition or in the alternative, control module (12) may be removed for servicing, testing, replacement, or any other purpose.

In some versions, control module (12) and/or power source (14) are incorporated into a handpiece of surgical instrument (10), such that surgical instrument (10) is readily portable and "tethereless". In some other versions, control module (12) and/or power source (14) are separate from surgical instrument (10), and are coupled with surgical instrument (10) via a cable. By way of example only, control module (12) and/or power source (14) may be provided through an ultrasonic generator unit as described in U.S. Pub. No. 2011/0087212, entitled "Surgical Generator for Ultrasonic and Electrosurgical Devices," published Apr. 14, 2011, the disclosure of which is incorporated by reference herein. Still other various ways in which control module (12) and power source (14) may be provided will be apparent to those of ordinary skill in the art in view of the teachings herein.

End effector (16) is coupled to control module (12) and/or other components by another electrical connection (22). End effector (16) is configured to perform a desired function of surgical instrument (10). By way of example only, such function may include cauterizing tissue, ablating tissue, severing tissue, ultrasonically vibrating, stapling tissue, or any other desired task for surgical instrument (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. As will be described in greater detail below, end effector (16) may also be removable from surgical instrument (10) for servicing, testing, replacement, or any other purpose as will be apparent to one of ordinary skill in the art in view of the teachings herein. In some versions, end effector (16) is modular such that surgical instrument (10) may be used with different kinds of end effectors (e.g., as taught in U.S. Provisional Application Ser. No. 61/410,603, etc.). Various other configurations of end effector (16) and uses for end effector (16) will be apparent to those of ordinary skill in the art in view of the teachings herein.

Surgical instrument (10) of the present example includes a trigger (18) and a sensor (20), though it should be understood that such components are merely optional. Trigger (18) may include a variety of components and/or features, including but not limited to a pivoting squeeze trigger, one or more buttons, one or more knobs or dials, one or more sliders, etc. Trigger (18) is coupled to control module (12) and power source (14) by electrical connection (22). Trigger (18) may be configured to selectively provide power from power source (14) to end effector (16) (and/or to some other component of surgical instrument (10)) to activate surgical instrument (10) when performing a procedure. In some versions where control module (12) is omitted, trigger (18) simply serves as a switch to selectively complete a circuit between power source (14) and end effector (16). Sensor (20) is also coupled to control module (12) by an electrical connection (22) and may be configured to provide a variety of information to control module (12) during a procedure. By way of example only, such configurations may include sensing a temperature at end effector (16), sensing the impedance of tissue adjacent to end effector (16), determining the oscillation rate of end effector (16), etc. Data from sensor (20) may be processed by control module (12) to affect the delivery of power to end effector (16) (e.g., in a feedback loop, etc.). Various other configurations of sensor (20) and uses for sensor (20) will be apparent to those of ordinary skill in the art in view of the teachings herein. Of course, as with other components described herein, surgical instrument (10) may have more than one sensor (20), or sensor (20) may simply be omitted if desired.

Merely illustrative variations of surgical instrument (10) may take will be described in greater detail below. It should therefore be understood that any of the above teachings may be readily combined with any of the teachings below. It should also be understood that any of the teachings herein may be readily combined with any of the teachings in any of the references cited herein. Various suitable ways in which such teachings may be combined will be apparent to those of ordinary skill in the art in view of the teachings herein. All such modifications and variations are intended to be included within the scope of the claims.

II. Exemplary Surgical Instrument with Breech Style Coupling for Removable Shaft Assembly FIGS. 2-3 depicts a merely exemplary form that surgical instrument (100) may take. In particular, FIGS. 2-3 show a surgical instrument (100) comprising a reusable handle assembly (102), a shaft assembly (110), and a power source connector (106). In the some versions, the power source may be located internally within a disposable or reusable handle assembly (102) of surgical instrument (100). Alternatively, the power source (not shown) may only partially extend into disposable or reusable handle assembly (102) and may be selectively attachable to a portion of disposable or reusable handle assembly (102). In yet a further exemplary configuration, a portion of disposable or reusable handle assembly (102) may extend into power source (not shown) and power source (not shown) may be selectively attachable to the portion of disposable or reusable handle assembly (102). In some versions, an internal or external removable power source (not shown) may also be configured to detach from surgical instrument (100) and decouple from control module (not shown) or power source connector (106). As a result, the internal or external removable power source (not shown) may be completely separated from surgical instrument (100) in some versions. In the present example, the power source comprises a generator configured in accordance with the teachings of U.S. Pub. No. 2011/0087212; and power source connector (106) comprises a cable. While surgical instrument (100) comprises a harmonic/ultrasonic instrument in the present example, it should be understood that surgical instrument (100) may alternatively comprise an RF instrument and/or various other kinds of instrument. It should be understood that surgical instrument (100) may be constructed and operable in accordance with surgical instrument (10) and/or in accordance with at least some of the teachings of any of the references cited herein. Various other kinds of devices to which the teachings of surgical instrument (100) may be applied will be apparent to those of ordinary skill in the art in view of the teachings herein.

Handle assembly (102) of the present example comprises a pistol grip (103), a pivoting trigger (105), and a pair of buttons (107). Pivoting trigger (105) is operable to selectively actuate a pivoting clamp pad of an end effector as will be described in greater detail below. Buttons (107) are operable to selectively activate a harmonic blade of the end effector as will also be described in greater detail below. For instance, one button (107) may activate the harmonic blade at a higher power level while the other button (107) may activate the harmonic blade at a lower power level. Handle assembly (102) also includes a transducer (108). Transducer (108) is coupled with cable (106) and comprises a plurality of piezoelectric elements that are configured to convert electrical power from cable (106) into ultrasonic vibrations. These vibrations are transmitted to a distal threaded member (109), which is configured to acoustically couple with a waveguide of shaft assembly (110) as will be described in greater detail below. An integral torque knob (140) is operable to rotate transducer (108) to secure the engagement between distal threaded member (109) and the waveguide of shaft assembly (110). Handle assembly (102) also includes a transverse bar (118) and a resilient locking tab (124) for engaging shaft assembly (112).

Shaft assembly (110) of the present example comprises a shaft (110) extending distally from a casing (113), which further includes an attachment hook (116). The distal end of shaft assembly (110) includes an end effector (not shown), which includes the pivoting clamp pad and harmonic blade referred to above. Examples of these components are taught in various references cited herein. For instance, a waveguide (not shown) may extend coaxially through shaft assembly (110) to acoustically couple the harmonic blade with distal threaded member (109) of transducer (108), thereby transmitting ultrasonic vibrations from transducer (108) to the harmonic blade. A secondary tube (not shown) is slidably and coaxially disposed about the waveguide, and is thus slidably and coaxially disposed within shaft (110). This secondary tube translates within shaft (110) to selectively pivot the clamp pad toward and away from the harmonic blade. The proximal end of the secondary tube is coupled with a force limiting mechanism (130), which is configured to engage a yoke (128) of handle assembly (102) as will be described in greater detail below. Force limiting mechanism (130) of shaft assembly (110) may comprise a wave spring mechanism, a double wave spring mechanism, and/or any other suitable structure. Yoke (128) is coupled with pivoting trigger (105), such that yoke (128) translates in response to trigger (105) pivoting toward and away from grip (103). This engagement thus provides pivoting of the clamp pad in response to pivoting of trigger (105).

To connect shaft assembly (110) to the handle assembly (102), the user places attachment hook (116) onto transverse bar (118) and rotates upwardly or clockwise the proximal end of shaft assembly (110) until locking detent (120) of shaft assembly (110) snaps into engagement with locking tab (124) of handle assembly (102). At this point, a groove (126) of force limiting mechanism (130) is received in yoke (128) of handle assembly (102). Movement of trigger (105) now causes corresponding motion in force limiting mechanism (130) of surgical shaft assembly (110), which in turn causes pivoting movement of the clamp pad in the end effector. The user then pushes torque knob (140) forward and rotates it so that distal threaded member (109) readily attaches to the proximal end of the waveguide of shaft assembly (110), acoustically coupling transducer assembly (108) to the waveguide of shaft assembly (110). In some versions, torque knob (140) includes features providing functionality similar to that of a torque wrench, whereby such features ensure ideal acoustic continuity by permitting the coupling to have sufficient torque while preventing the coupling from having too much torque. By way of example only, torque knob (140) may include features that provide two clicks when transducer assembly (108) is coupled to the waveguide with an appropriate amount of torque, thereby providing audible and/or tactile feedback to the user. It should also be understood that connector (106) may be coupled to torque knob (140) in a manner such that connector (106) rotates with torque knob (140). Alternatively, connector (106) may remain stationary as torque knob (140) and transducer (108) rotate. In such versions, connector (106) may be coupled with transducer (108) via a commutator, slip ring assembly, and/or other types of features. As another merely illustrative example, rotation knob (112) may be configured to provide such limiting of torque. As yet another merely illustrative example, a disposable torque wrench could couple transducer assembly (108) and surgical shaft assembly (110) to the distal end of handle assembly (102) in a conventional manner, as will be apparent to one of ordinary skill in the art in view of the teachings herein. Of course, the connection may alternatively be one that does not provide torque limiting.

It should also be understood that a cam or other feature may be provided to advance transducer assembly (108) toward shaft assembly (110) or vice versa, such that torque knob (140) need not necessarily be pushed forward to linearly engage torque assembly with shaft assembly (110). For instance, torque knob (140) may be coupled with a worm gear, rack and pinion system, and/or other type of feature that linearly drives transducer assembly (108) distally in response to rotation of torque knob (140). Such distal movement may be concomitant with rotation of transducer assembly (108). As another merely illustrative alternative, a mechanism may provide staged movement, such that rotation of torque knob (140) initially just translates transducer assembly (108) then just rotates transducer assembly (108) after transducer assembly (108) has been translated an appropriate distance.

As will be apparent to one of ordinary skill in the art in view of the teachings herein, the configuration of surgical instrument (100) provides for the selective coupling of a reusable or disposable shaft assembly (110) to disposable or reusable handle assembly (102). To replace a shaft assembly (110), the user may simply rotate torque knob (140) in the opposite direction to de-couple distal threaded member (109) from the waveguide of shaft assembly (110); then depress locking tab (124) to disengage detent (120); then rotate shaft assembly (110) downward to remove hook (116) from transverse bar (118). In some other versions, the casing (113) of shaft assembly (110) may be reusable with only the remaining portion of shaft assembly (110) needing to be selectively coupled to the disposable or reusable handle assembly (102). For instance, attachment hook (116) and transverse bar (118) may form a permanent hinge that would provide for the surgical shaft assembly (110) to open but stay connected to the disposable or reusable handle assembly (102). At this point, the user would remove shaft (112) and drop in another disposable or reusable shaft (112), rotate casing (113) into position and couple the shaft (112) to handle assembly (102). As another merely illustrative variation, the user may simply withdraw the waveguide and blade from shaft assembly (110) when shaft assembly (110) is rotated downward, without removing shaft assembly (110) from handle assembly (102), and slide another waveguide and blade into shaft assembly (110). Other suitable variations will be apparent to those of ordinary skill in the art in view of the teachings herein.

III. Exemplary Surgical Instrument with Removable Shaft Assembly Having Integral Pivot Bar FIGS. 4-5 show another exemplary surgical instrument (200) that includes a reusable handle assembly (204), a shaft assembly (214), and a cable (202). As in surgical instrument (100) described above, the power source for surgical instrument (200) may be internal or external to surgical instrument (200). Similarly, while surgical instrument (200) comprises a harmonic/ultrasonic instrument in the present example, it should be understood that surgical instrument (200) may alternatively comprise an RF instrument and/or various other kinds of instrument. It should further be understood that surgical instrument (200) may be constructed and operable in accordance with surgical instrument (10) and/or in accordance with at least some of the teachings of any of the references cited herein. Various other kinds of devices to which the teachings of surgical instrument (200) may be applied will be apparent to those of ordinary skill in the art in view of the teachings herein.

Handle assembly (204) of the present example comprises a pistol grip (203), a pivoting trigger (205), and a pair of buttons (216). Pivoting trigger (205) is operable to selectively actuate a pivoting clamp pad of an end effector as will be described in greater detail below. Buttons (216) are operable to selectively activate a harmonic blade of the end effector as will also be described in greater detail below. For instance, one button (216) may activate the harmonic blade at a higher power level while the other button (216) may activate the harmonic blade at a lower power level. Handle assembly (204) also includes a transducer (220). Transducer (220) is coupled with cable (202) and comprises a plurality of piezoelectric elements that are configured to convert electrical power from cable (202) into ultrasonic vibrations. These vibrations are transmitted to a distal threaded member (240), which is configured to acoustically couple with a waveguide of shaft assembly (214) as will be described in greater detail below. An integral torque knob (230) is operable to rotate transducer (220) to secure the engagement between distal threaded member (240) and the waveguide of shaft assembly (214). Handle assembly (204) also includes a receiving notch (238) and yoke (207) for engaging shaft assembly (214).

Shaft assembly (214) of the present example comprises a shaft (208) extending distally from a knob (222). The distal end of shaft assembly (214) includes an end effector (not shown), which includes the pivoting clamp pad and harmonic blade referred to above. Examples of these components are taught in various references cited herein. For instance, a waveguide (not shown) may extend coaxially through shaft assembly (214) to acoustically couple the harmonic blade with distal threaded member (240) of transducer (220), thereby transmitting ultrasonic vibrations from transducer (220) to the harmonic blade. A secondary tube (not shown) is slidably and coaxially disposed about the waveguide, and is thus slidably and coaxially disposed within shaft (208). This secondary tube translates within shaft (208) to selectively pivot the clamp pad toward and away from the harmonic blade. The proximal end of the secondary tube is coupled with a force limiting mechanism (236), which is configured to engage a yoke (207) of handle assembly (204) as will be described in greater detail below. Force limiting mechanism (236) of shaft assembly (214) may comprise a wave spring mechanism, a double wave spring mechanism, and/or any other suitable structure. Yoke (207) is coupled with pivoting trigger (205), such that yoke (207) translates in response to trigger (205) pivoting toward and away from grip (203). This engagement thus provides pivoting of the clamp pad in response to pivoting of trigger (205). Shaft assembly (214) also includes a pivot bar (224), which is removably received in notch (238) of handle assembly (204).

To connect shaft assembly (214) to transducer assembly (220), the user positions pivot bar (224) into receiving notch (238) and then utilizes pivot bar (224) to rotate shaft assembly (210) clockwise until force limiting mechanism (236) mates with yoke (207). In particular, yoke (207) encompasses groove (234) of force limiting mechanism (236). Movement of trigger (205) now causes corresponding motion in force limiting mechanism (236) of surgical shaft assembly (214), which in turn causes pivoting movement of the clamp pad in the end effector. After force limiting mechanism (236) is positioned in yoke (207), the user then manipulates torque knob (230) to couple distal threaded member (240) of transducer (220) with the proximal end of the waveguide of shaft assembly (214), acoustically coupling transducer assembly (220) to the waveguide of shaft assembly (214). As in surgical instrument (100), torque knob (230) may include features similar to that of a torque wrench, a separate torque wrench may be used, such features may be otherwise provided, or such features may simply be omitted. By way of example only, torque knob (230) may include features that provide two clicks when transducer assembly (220) is coupled to the waveguide with an appropriate amount of torque, thereby providing audible and/or tactile feedback to the user. It should also be understood that torque knob (230) may be pushed forward to drive transducer (220) toward shaft assembly (214) in some versions; or a cam or other feature may be provided to advance transducer assembly (220) toward shaft assembly (214) or vice versa. While not shown, some versions of handle assembly (204) may include an integral sliding cover that slides over the coupled proximal end of shaft assembly (214) and distal end of handle assembly (204), protecting the components therein from debris, etc., during use of surgical instrument. Alternatively a snap-on cap, shield, or other feature may be provided to cover these regions.

It should also be understood that a cam or other feature may be provided to advance transducer assembly (220) toward shaft assembly (214) or vice versa, such that torque knob (230) need not necessarily be pushed forward to linearly engage torque assembly with shaft assembly (214). For instance, torque knob (230) may be coupled with a worm gear, rack and pinion system, and/or other type of feature that linearly drives transducer assembly (220) distally in response to rotation of torque knob (230). Such distal movement may be concomitant with rotation of transducer assembly (220). As another merely illustrative alternative, a mechanism may provide staged movement, such that rotation of torque knob (230) initially just translates transducer assembly (220) then just rotates transducer assembly (220) after transducer assembly (220) has been translated an appropriate distance.

As will be apparent to one of ordinary skill in the art in view of the teachings herein, the configuration of surgical instrument (200) provides for the selective coupling of a reusable or disposable shaft assembly (214) to disposable or reusable handle assembly (204). By way of example only, if the blade of shaft assembly (214) and/or transducer (220) were to have an error during the set up because the torque was inadequate, handle assembly (204) and/or shaft assembly (214) could be replaced. To replace a shaft assembly (214), the user may simply rotate torque knob (230) in the opposite direction to de-couple distal threaded member (240) from the waveguide of shaft assembly (214); then rotate shaft assembly (214) downward to remove pivot bar (224) from notch (238). Other suitable variations will be apparent to those of ordinary skill in the art in view of the teachings herein.

IV. Exemplary Surgical Instruments with Drop-in Removable Shaft Assembly and Pivoting Cover FIGS. 6-7 show another exemplary surgical instrument (300) that includes a reusable handle assembly (304), a shaft assembly (314), and a cable (302). As in surgical instrument (100) described above, the power source for surgical instrument (300) may be internal or external to surgical instrument (300). Similarly, while surgical instrument (300) comprises a harmonic/ultrasonic instrument in the present example, it should be understood that surgical instrument (300) may alternatively comprise an RF instrument and/or various other kinds of instrument. It should further be understood that surgical instrument (300) may be constructed and operable in accordance with surgical instrument (10) and/or in accordance with at least some of the teachings of any of the references cited herein. Various other kinds of devices to which the teachings of surgical instrument (300) may be applied will be apparent to those of ordinary skill in the art in view of the teachings herein.

Handle assembly (304) of the present example comprises a pistol grip (303), a pivoting trigger (305), and a pair of buttons (316). Pivoting trigger (305) is operable to selectively actuate a pivoting clamp pad of an end effector as will be described in greater detail below. Buttons (316) are operable to selectively activate a harmonic blade of the end effector as will also be described in greater detail below. For instance, one button (316) may activate the harmonic blade at a higher power level while the other button (316) may activate the harmonic blade at a lower power level. Handle assembly (304) also includes a transducer (not shown). The transducer is coupled with cable (302) and comprises a plurality of piezoelectric elements that are configured to convert electrical power from cable (302) into ultrasonic vibrations. These vibrations are transmitted to a distal threaded member (not shown), which is configured to acoustically couple with a waveguide of shaft assembly (314) as will be described in greater detail below. An integral torque knob (330) is operable to rotate the transducer to secure the engagement between the distal threaded member and the waveguide of shaft assembly (314). Handle assembly (304) also includes a distal notch (338) and upper open portion (339) for receiving shaft assembly (314); as well as a yoke (not shown) and pivoting cover (350) for engaging shaft assembly (314). In this example, pivoting cover (350) pivots about an axis that is parallel to the longitudinal axis of shaft assembly (314).

Shaft assembly (314) of the present example comprises a shaft (308) extending distally from a knob (309). The distal end of shaft assembly (314) includes an end effector (not shown), which includes the pivoting clamp pad and harmonic blade referred to above. Examples of these components are taught in various references cited herein. For instance, a waveguide (not shown) may extend coaxially through shaft assembly (314) to acoustically couple the harmonic blade with the distal threaded member of the transducer of handle assembly (304), thereby transmitting ultrasonic vibrations from the transducer to the harmonic blade. A secondary tube (not shown) is slidably and coaxially disposed about the waveguide, and is thus slidably and coaxially disposed within shaft (308). This secondary tube translates within shaft (308) to selectively pivot the clamp pad toward and away from the harmonic blade. The proximal end of the secondary tube is coupled with a force limiting mechanism (336), which is configured to engage a yoke (not shown) of handle assembly (304) as will be described in greater detail below. Force limiting mechanism (336) of shaft assembly (314) may comprise a way spring mechanism, a double wave spring mechanism, and/or any other suitable structure. The yoke is coupled with pivoting trigger (305) as described elsewhere herein, such that the yoke translates in response to trigger (305) pivoting toward and away from grip (303). This engagement thus provides pivoting of the clamp pad in response to pivoting of trigger (305).

To connect shaft assembly (314) to handle assembly (304) and to the transducer assembly therein, the user positions the proximal portion of shaft assembly (314) in distal notch (338) and upper open portion (339) of handle assembly (304). In this example, the proximal portion of shaft assembly (314) includes all features located proximal to knob (309). The user then presses downwardly to seat force limiting mechanism (336) in the yoke of handle assembly (304), such that the yoke encompasses groove (334) of force limiting mechanism (336). Next, the user moves pivot cover (350) to a closed position. Movement of trigger (305) now causes corresponding motion in force limiting mechanism (336) of shaft assembly (314), which in turn causes pivoting movement of the clamp pad in the end effector. After force limiting mechanism (336) is positioned in the yoke, the user then manipulates torque knob (330) to couple the distal threaded member of the transducer in handle assembly (304) with the proximal end of the waveguide of shaft assembly (314), acoustically coupling the transducer assembly to the waveguide of shaft assembly (314). As in surgical instrument (100), torque knob (330) may include features similar to that of a torque wrench, a separate torque wrench may be used, such features may be otherwise provided, or such features may simply be omitted. By way of example only, torque knob (330) may include features that provide two clicks when the transducer is coupled to the waveguide with an appropriate amount of torque, thereby providing audible and/or tactile feedback to the user. It should also be understood that torque knob (330) may be pushed forward to drive the transducer toward shaft assembly (314) in some versions; or a cam, worm gear, rack and pinion, and/or other feature may be provided to advance the transducer assembly toward shaft assembly (314) or vice versa. Before or after the acoustic coupling is completed, the user pivots cover (350) closed to retain and/or protect the proximal end of shaft assembly (314).

FIG. 7 shows a merely illustrative variation of surgical instrument (300). In this version, the components and features described above are the same except that in this example, handle assembly (304) includes a laterally opening notch (337) and a laterally presented open portion (341) instead of a vertically opening notch (338) and upwardly presented open portion (339). In addition, handle assembly (304) in this example includes a vertically movable yoke (340) that is moved by a release slider (342). Yoke (340) generally defines an upwardly oriented "U" shape in this example. Thus, this version of surgical instrument (300) operates similar to the version shown in FIG. 6, except in how shaft assembly (314) is coupled with handle assembly (304). In this version, slider (342) is moved downwardly to move yoke (340) downwardly out of its default position. In some versions, yoke (340) is resiliently biased to the upper, default position shown in FIG. 7, such that yoke (340) will return to that position upon release of slider (342). With yoke (340) moved out of position, the proximal end of shaft assembly (314) is pushed laterally into notch (337) and open portion (341). Slider (342) is then released to couple yoke (340) with force limiting mechanism (336) of shaft assembly (314). In addition, the user manipulates torque knob (330) to couple the transducer of handle assembly (304) with the waveguide of shaft assembly (314). The user also pivots cover (351) closed to retain and/or protect the proximal end of shaft assembly (314). In an exemplary variation of this example, yoke (340) generally defines a horizontally oriented "U" shape, such that yoke (340) does not need to be moved downwardly to provide clearance for entry of the proximal end of shaft assembly (314) into notch (337). In other words, proximal end of shaft assembly (314) may simply be inserted directly into yoke (340) via notch (337); and slider (342) may be omitted.

As will be apparent to one of ordinary skill in the art in view of the teachings herein, the configuration of surgical instrument (300) provides for the selective coupling of a reusable or disposable shaft assembly (314) to disposable or reusable handle assembly (304). By way of example only, if the blade of shaft assembly (314) and/or the transducer were to have an error during the set up because the torque was inadequate, handle assembly (304) and/or shaft assembly (314) could be replaced. To replace a shaft assembly (314), the user may simply rotate torque knob (330) in the opposite direction to de-couple the distal threaded member of the transducer from the waveguide of shaft assembly (314), open cover (350, 351), then pull shaft assembly (314) in a transverse direction to remove from handle assembly (304). In the version shown in FIG. 7, the user would also pull slider (342) down to disengage yoke (340) from force limiting mechanism (236) before pulling shaft assembly (314) from handle assembly (304). Other suitable variations will be apparent to those of ordinary skill in the art in view of the teachings herein.

Figure 10:
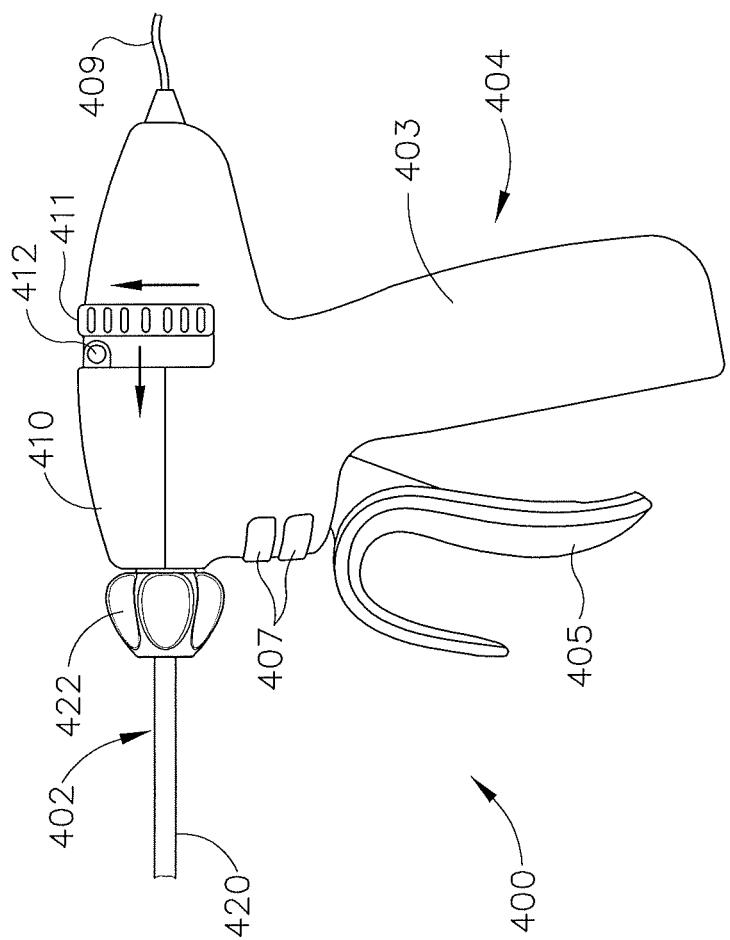
FIG. 10 depicts a partial side view of the surgical instrument of FIG. 8, with the shaft assembly seated in the handle assembly and secured to the handle assembly.

FIGS. 8-10 show yet another exemplary surgical instrument (400) that includes a shaft assembly (402), a handle assembly (404), a transducer assembly (not shown), and a cable (409). As in surgical instrument (100) described above, the power source for surgical instrument (400) may be internal or external to surgical instrument (400). Similarly, while surgical instrument (400) comprises a harmonic/ultrasonic instrument in the present example, it should be understood that surgical instrument (400) may alternatively comprise an RF instrument and/or various other kinds of instrument. It should further be understood that surgical instrument (400) may be constructed and operable in accordance with surgical instrument (10) and/or in accordance with at least some of the teachings of any of the references cited herein. Various other kinds of devices to which the teachings of surgical instrument (400) may be applied will be apparent to those of ordinary skill in the art in view of the teachings herein.

Handle assembly (404) of the present example comprises a pistol grip (403), a pivoting trigger (405), and a pair of buttons (407). Pivoting trigger (405) is operable to selectively actuate a pivoting clamp pad of an end effector as will be described in greater detail below. Buttons (407) are operable to selectively activate a harmonic blade of the end effector as will also be described in greater detail below. For instance, one button (407) may activate the harmonic blade at a higher power level while the other button (407) may activate the harmonic blade at a lower power level. Handle assembly (404) also includes a transducer (not shown). The transducer is coupled with cable (409) and comprises a plurality of piezoelectric elements that are configured to convert electrical power from cable (409) into ultrasonic vibrations. These vibrations are transmitted to a distal threaded member (not shown), which is configured to acoustically couple with a waveguide of shaft assembly (402) as will be described in greater detail below. An integral torque knob (411) is operable to rotate the transducer to secure the engagement between the distal threaded member and the waveguide of shaft assembly (402). Handle assembly (404) also includes a recess (416) for receiving shaft assembly (402); as well as a yoke (408) and pivoting cover (410) for engaging shaft assembly (402). In this example, pivoting cover (410) pivots about an axis that is perpendicular to the longitudinal axis of shaft assembly (402).

Shaft assembly (402) of the present example comprises a shaft (420) extending distally from a knob (422). The distal end of shaft assembly (402) includes an end effector (not shown), which includes the pivoting clamp pad and harmonic blade referred to above. Examples of these components are taught in various references cited herein. For instance, a waveguide (not shown) may extend coaxially through shaft assembly (402) to acoustically couple the harmonic blade with the distal threaded member of the transducer of handle assembly (404), thereby transmitting ultrasonic vibrations from the transducer to the harmonic blade. A secondary tube (not shown) is slidably and coaxially disposed about the waveguide, and is thus slidably and coaxially disposed within shaft (420). This secondary tube translates within shaft (420) to selectively pivot the clamp pad toward and away from the harmonic blade. The proximal end of the secondary tube is coupled with a force limiting mechanism (424), which is configured to engage yoke (408) of handle assembly (404) as will be described in greater detail below. Force limiting mechanism (424) of shaft assembly (402) may comprise a way spring mechanism, a double wave spring mechanism, and/or any other suitable structure. The yoke is coupled with pivoting trigger (405) as described elsewhere herein, such that the yoke translates in response to trigger (405) pivoting toward and away from grip (403). This engagement thus provides pivoting of the clamp pad in response to pivoting of trigger (405).

To connect shaft assembly (402) to handle assembly (404) and to the transducer assembly therein, and with cover (410) pivoted to an open position, the user positions the proximal portion of shaft assembly (402) in recess (416) of handle assembly (404). In this example, the proximal portion of shaft assembly (402) includes all features located proximal to knob (422). The user then presses downwardly to seat force limiting mechanism (424) in yoke (408) of handle assembly (404), such that yoke (408) encompasses groove (426) of force limiting mechanism (424). Movement of trigger (405) now causes corresponding motion in force limiting mechanism (424) of shaft assembly (314), which in turn causes pivoting movement of the clamp pad in the end effector. After force limiting mechanism (424) is positioned in yoke (416), the user then manipulates torque knob (411) to couple the distal threaded member of the transducer in handle assembly (404) with the proximal end of the waveguide of shaft assembly (402), acoustically coupling the transducer assembly to the waveguide of shaft assembly (402). As in surgical instrument (100), torque knob (411) may include features similar to that of a torque wrench, a separate torque wrench may be used, such features may be otherwise provided, or such features may simply be omitted. By way of example only, torque knob (411) may include features that provide two clicks when the transducer is coupled to the waveguide with an appropriate amount of torque, thereby providing audible and/or tactile feedback to the user. It should also be understood that torque knob (411) may be pushed forward to drive the transducer toward shaft assembly (402) in some versions; or a cam, worm gear, rack and pinion, and/or other feature may be provided to advance the transducer assembly toward shaft assembly (402) or vice versa.

In some versions, the user pivots cover (410) closed to retain and/or protect the proximal end of shaft assembly (402) before or after the transducer is coupled with the waveguide of shaft assembly (402). In some other versions, torque knob (411) is further configured to close cover (410) while torque knob (411) couples the transducer with the waveguide of shaft assembly (402), such that the two acts are performed substantially simultaneously. In addition, some versions of torque knob (411) are configured to cover hinge (412) of cover (410) upon coupling of the transducer with the waveguide of shaft assembly (402). For instance, a cam or other feature may advance torque knob (411) distally when torque knob (411) is rotated sufficiently to couple the transducer with the waveguide of shaft assembly (402). Positioning at least part of torque knob (411) over hinge (412) may prevent cover (410) from being opened while the transducer is coupled to the waveguide of shaft assembly (402). Other suitable variations will be apparent to those of ordinary skill in the art in view of the teachings herein.

VII. Exemplary Handle Assembly Providing Separation of Mechanical Features from Electrical Features In some instances, it may be desirable to provide modularity of mechanical components of a surgical instrument (10) in an integral fashion with a shaft assembly. In other words, it may be desirable for a shaft assembly and all related mechanical components to be readily removable from non-mechanical components of a surgical instrument (10). In some such versions, the non-mechanical components of the surgical instrument (10) may include electrical components such as a portable power source (e.g., battery, etc.), a control module (e.g., one or more printed circuit boards with integral components, etc.), and/or other types of components. In some such versions, the non-mechanical components of the surgical instrument (10) may be provided as a re-usable unit and/or re-usable components; while the mechanical components may be provided as a replaceable and/or disposable unit (and/or as replaceable components and/or replaceable components).

Figure 11:
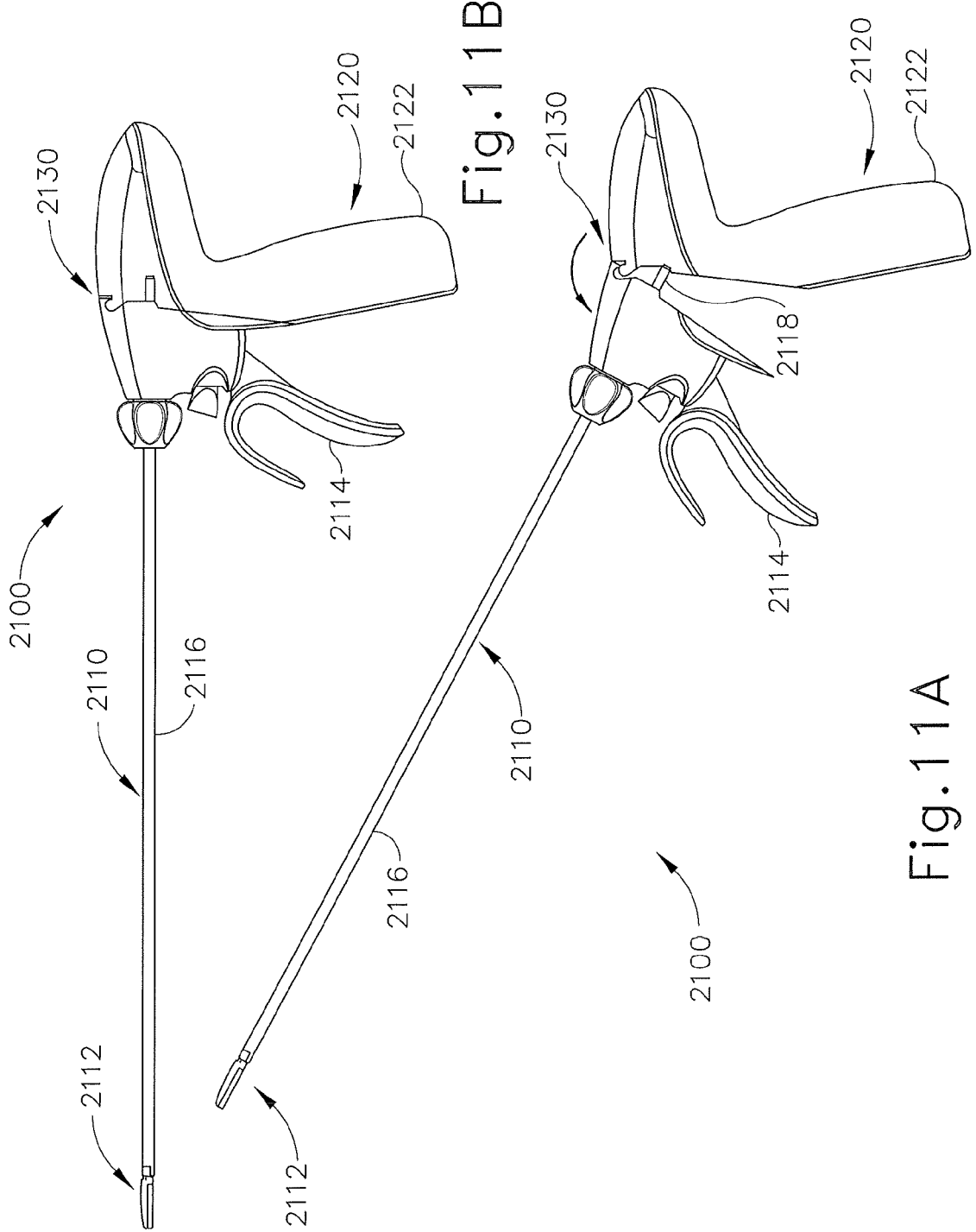
FIG. 11A depicts an exemplary alternative surgical instrument with a mechanical portion separated from an electrical portion.
FIG. 11B depicts the surgical instrument of FIG. 11A with the mechanical portion coupled with the electrical portion.
Figure 12:
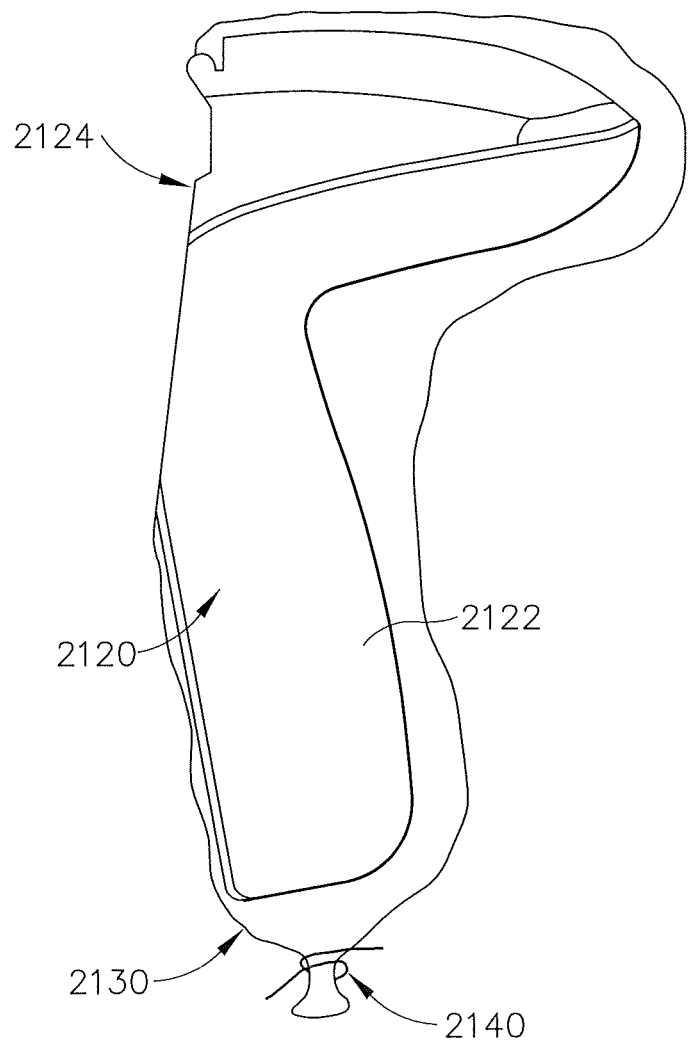
FIG. 12 depicts the electrical portion of the surgical instrument of FIG. 11A with a sterile bag.

FIGS. 11-12 show an example of a surgical instrument (2100) that is provided as a first module (2110) and a second module (2120). First module (2110) includes an end effector (2112) that is actuated by a trigger (2114) and that is disposed at the distal end of a shaft (2116). First module (2110) includes all of the mechanical components necessary to convert actuation of trigger (2114) into actuation of end effector (2112). In versions where instrument (2110) comprises an ultrasonic instrument, first module (2110) may further include a waveguide and other features that will be apparent to those of ordinary skill in the art in view of the teachings herein. In versions where instrument (2110) comprises an RF electrosurgical instrument, first module (2110) may further include a firing beam and other features that will be apparent to those of ordinary skill in the art in view of the teachings herein. In the present example, first module (2110) also includes a proximal shaft portion (2118) that is configured to engage electronic components of second module (2120). For instance, proximal shaft portion (2118) may include one or more electrical contacts, electrodes, etc.

Second module (2120) of the present example includes a pistol grip (2122) and houses a battery (not shown) and a control module (not shown). First module (2110) is operable to couple with second module (2120) through a pivotal coupling (2130). For instance, modules (2110, 2120) may first be joined at coupling (2130) as shown in FIG. 11A. First module (2110) may then be pivoted toward second module (2120) to the position shown in FIG. 11B. This pivoting motion will ultimately seat proximal shaft portion (2118) in a complementary feature of second module (2120), providing electrical communication between modules (2110, 2120). One or more locking features may be provided to secure modules (2110, 2120) together in the position shown in FIG. 11B. For instance, modules (2110, 2120) may include complementary snap fit features. In addition or in the alternative, one or more clips, clamps, straps, rings, and/or other features may be used to secure modules (2110, 2120) together in the position shown in FIG. 11B. In the present example, surgical instrument (2100) is fully operable once modules (2110, 2120) are secured together as shown in FIG. 11B.

In some versions, second module (2120) is provided as a reusable component. It should therefore be understood that second module (2120) may be sterilized between uses of instrument (2100), through various sterilization techniques as will be apparent to those of ordinary skill in the art in view of the teachings herein. After being sterilized and before being used, second module (2120) may be placed in a sterile bag (2130) as shown in FIG. 12. Bag (2130) may be closed via a tie (2140) and/or using any other suitable components/features/techniques. As also shown in FIG. 12, bag (2130) is bonded to an interface region (2124) of second module (2120). Such bonding may be performed using heat sealing, an adhesive, and/or in any other suitable fashion. In some versions, a new and/or otherwise sterile first module (2110) is coupled with second module (2120) while bag (2130) is still secured to second module (2120). For instance, proximal shaft portion (2118) and/or other features of first module (2110) may pierce bag (2130) when first module (2110) pivoted into place as shown in the transition from FIG. 11A to FIG. 11B. At least part of bag (2130) may be removed from second module (2120) after modules (2110, 2120) are coupled together. In addition or in the alternative, at least part of bag (2130) may be removed before modules (2110, 2120) are coupled together. As yet another merely illustrative variation, second module (2120) may always be used with a fresh bag (2130), such that second module (2120) is not sterilized between uses, and such that bag (2130) is simply replaced between uses in lieu of sterilizing second module (2120).

VIII. Miscellaneous

While certain configurations of exemplary surgical instruments (10, 100, 200, 300, 400) have been described, various other ways in which surgical instruments (10, 100, 200, 300, 400) may be configured will be apparent to those of ordinary skill in the art in view of the teachings herein. By way of example only, surgical instruments (10, 100, 200, 300, 400) and/or any other surgical instrument referred to herein may be constructed in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,500, 176; U.S. Pat. No. 6,783,524; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pat. No. 7,416, 101; U.S. Pat. No. 7,738,971; U.S. Pub. No. 2006/0079874; U.S. Pub. No. 2007/0191713; U.S. Pub. No. 2007/0282333; U.S. Pub. No. 2008/0200940; U.S. Pub. No. 2009/0143797 (now U.S. Pat. No. 8,419,757); U.S. Pub. No. 2009/0209990 (now U.S. Pat. No. 8,957,174); U.S. Pub. No. 2010/0069940; U.S. Pub. No. 2011/0015660 (now U.S. Pat. No. 8,461,744); U.S. Pat. Pub. No. 2011/0087218 (now U.S. Pat. No. 8,939, 974); U.S. patent application Ser. No. 13/151,481, published as U.S. Pub. No. 2012/0116379; and/or U.S. Provisional Application Ser. No. 61/410,603. The disclosures of each of those documents are incorporated by reference herein in their entirety.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The teachings, expressions, embodiments, examples, etc. herein should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body; and
   (b) a shaft assembly configured to removably couple with the body, wherein the shaft assembly comprises:
      (i) an end effector, and
      (ii) an acoustic transmission member in communication with the end effector, wherein the acoustic transmission member defines a longitudinal axis;
   wherein one or both of the body or the shaft assembly includes a pivot feature, wherein the pivot feature is operable to pivot the shaft assembly about an axis perpendicular to the longitudinal axis of the acoustic transmission member between an unsecured position and a secured position, wherein the pivot feature in the secured position is operable to secure the shaft assembly to the body such that the acoustic transmission member is positioned to transmit energy to the end effector, wherein the pivot feature in the unsecured position is configured to disconnect the transmission member from the energy source.

2. The surgical instrument of claim 1, further comprising an activation member, wherein the activation member includes a button, wherein the body comprises a handle including a grip, wherein the button of the activation member is integral with the handle of the body.

3. The surgical instrument of claim 1, wherein the acoustic transmission member is configured to removably couple to an energy source, wherein the energy source comprises an ultrasonic transducer operable to convert electrical power into ultrasonic vibrations, wherein the acoustic transmission member comprises a waveguide, wherein the end effector comprises a ultrasonic blade.

4. The surgical instrument of claim 1, wherein the acoustic transmission member is configured to removably couple to an energy source, wherein the energy source and the acoustic transmission member comprise complementary threading, wherein the body further comprises a torque knob operable to rotate the energy source to couple the energy source with the acoustic transmission member.

5. The surgical instrument of claim 4, wherein the torque knob is further operable to linearly advance the energy source toward the acoustic transmission member to engage threads of the energy source with complementary threads of the acoustic transmission member.

6. The surgical instrument of claim 1, wherein the pivot feature comprises a hook and a bar, wherein the hook is configured to engage the bar and pivot about the bar.

7. The surgical instrument of claim 6, wherein the hook is integral with the shaft assembly, wherein the bar is integral with the body.

8. The surgical instrument of claim 1, wherein the pivot feature comprises a bar and a notch, wherein the notch is configured to receive the bar, wherein the bar is configured to rotate within the notch.

9. The surgical instrument of claim 8, wherein the bar is integral with the shaft assembly, wherein the notch is integral with the body.

10. The surgical instrument of claim 1, wherein the pivot feature comprises a pivoting cover integral with the body, wherein the pivoting cover is configured to retain a proximal portion of the shaft assembly in a recess of the body.

11. The surgical instrument of claim 10, wherein the pivoting cover pivots about an axis that is perpendicular to the longitudinal axis defined by the shaft assembly.

12. The surgical instrument of claim 11, further comprising a hinge coupling the pivoting cover with the body, wherein the body further comprises a hinge covering feature operable to selectively cover the hinge to thereby retain the pivoting cover in a closed position.

13. The surgical instrument of claim 1, wherein the body comprises:
   (i) a first module, wherein the shaft assembly extends distally from the first module, wherein the first module further includes a user input feature operable to actuate a movable component of the end effector and one or more mechanical components coupling the user input feature with the movable component of the end effector, and
   (ii) a second module, wherein the second module contains an energy source.

14. The surgical instrument of claim 13, wherein the first module is removably coupled with the second module via the pivot feature, wherein the first module includes a feature configured to communicate with the energy source upon coupling of the first module with the second module, wherein the second module is provided in a sterile bag.

15. A surgical instrument, comprising:
   (a) a body including an ultrasonic transducer, wherein the ultrasonic transducer defines an axis;
   (b) a shaft assembly configured to removably couple with the body, wherein the shaft assembly comprises:
      (i) an end effector, the end effector including an ultrasonic blade, and
      (ii) a waveguide configured to removably couple with the transducer, wherein the waveguide is in communication with the ultrasonic blade, wherein the waveguide is configured to transmit energy from the transducer to the ultrasonic blade, wherein the waveguide defines a longitudinal axis;
   wherein one or both of the body or the shaft assembly includes a pivot feature, wherein the body is configured to receive the shaft assembly through an upper receiving portion of the body, wherein the upper receiving portion is shaped to complement the shaft assembly, wherein the pivot feature is operable to secure the shaft assembly to the body by pivoting the shaft assembly about an axis perpendicular to the longitudinal axis defined by the waveguide, wherein the shaft assembly is pivotable between a first pivotal position and a second pivotal position, wherein the waveguide is aligned with the axis of the transducer when the shaft assembly is in the first pivotal position, wherein the waveguide is in acoustic communication with the transducer when the shaft assembly is in the first pivotal position, wherein the waveguide is not aligned with the axis of the transducer when the shaft assembly is in the second pivotal position, wherein the waveguide is acoustically decoupled from the transducer when the shaft assembly is in the second pivotal position.

16. The surgical instrument of claim 15, further comprising a torque knob, wherein the torque knob is configured to linearly advance the transducer within the handle assembly and toward the waveguide.

17. A surgical instrument, comprising:
 (a) a body comprising a first portion and a second portion;
 (b) an ultrasonic energy source positioned within the first portion of the body; and
 (c) a shaft assembly rotatably secured to the second portion of the body, wherein the shaft assembly comprises:
  (i) an end effector, and
  (ii) an acoustic transmission member in communication with the end effector, wherein the acoustic transmission member defines a longitudinal axis;
 wherein one or both of the first portion or second portion of the body includes a pivot feature, wherein the pivot feature is operable to pivot the second portion of the body relative to the first portion of the body about an axis perpendicular to the longitudinal axis of the acoustic transmission member between an unsecured position and a secured position, wherein the shaft assembly is aligned with the ultrasonic energy source when the pivot feature is in the secured position, wherein the first portion and the second portion of the body together form a housing when the pivot feature is in the secured position, wherein the second portion of the body is decoupled from the first portion of the body when the pivot feature is in the unsecured position.

* * * * *